(12) United States Patent
Mennen

(10) Patent No.: US 10,358,413 B2
(45) Date of Patent: Jul. 23, 2019

(54) METHOD AND SYSTEM FOR THE INTEGRATED PRODUCTION OF UREA AND MELAMINE

(71) Applicant: Stamicarbon B.V., Sittard (NL)

(72) Inventor: Johannes Henricus Mennen, Sittard (NL)

(73) Assignee: Stamicarbon B.V., Sittard (NL)

( * ) Notice: Subject to any disclaimer, the term of this patent is extended or adjusted under 35 U.S.C. 154(b) by 0 days.

(21) Appl. No.: 15/568,795

(22) PCT Filed: Apr. 25, 2016

(86) PCT No.: PCT/NL2016/050291
§ 371 (c)(1),
(2) Date: Oct. 23, 2017

(87) PCT Pub. No.: WO2016/171562
PCT Pub. Date: Oct. 27, 2016

(65) Prior Publication Data
US 2018/0099926 A1    Apr. 12, 2018

(30) Foreign Application Priority Data
Apr. 23, 2015 (EP) .................................. 15164888

(51) Int. Cl.
*C07D 251/60* (2006.01)
*C07D 251/62* (2006.01)
*C07C 273/12* (2006.01)
*B01J 19/24* (2006.01)

(52) U.S. Cl.
CPC ........... *C07C 273/12* (2013.01); *B01J 19/245* (2013.01); *C07D 251/60* (2013.01); *C07D 251/62* (2013.01); *B01J 2219/00024* (2013.01); *B01J 2219/24* (2013.01); *Y02P 20/125* (2015.11)

(58) Field of Classification Search
CPC ............................ C07D 251/60; C07D 251/62
USPC .................................................. 544/201, 203
See application file for complete search history.

(56) References Cited

U.S. PATENT DOCUMENTS

| | | | |
|---|---|---|---|
| 3,239,522 A | * | 3/1966 | Cook .................... C07C 273/12 544/201 |
| 6,586,629 B1 | | 7/2003 | Coufal |
| 2007/0282102 A1 | * | 12/2007 | Brunengo ............. C07C 273/12 544/201 |

FOREIGN PATENT DOCUMENTS

| | | |
|---|---|---|
| EP | 1 716 111 | 12/2013 |
| WO | WO-98/08808 | 3/1998 |

OTHER PUBLICATIONS

International Search Report for PCT/NL2016/050291, dated Sep. 14, 2016, 3 pages.

* cited by examiner

*Primary Examiner* — Venkataraman Balasubramanian
(74) *Attorney, Agent, or Firm* — Morrison & Foerster LLP

(57) ABSTRACT

Disclosed is an integrated process for the production of urea and melamine, as well as a system for carrying out the process. The invention thereby pertains to an integrated process of the type wherein off-gas obtained from the production of melamine is entered into the process for the production of melamine, by condensation in the presence of water. A typical embodiment thereof is the condensation in the presence of an aqueous carbamate solution obtained from urea recovery. In accordance with the invention, said condensation takes place at a substantially lower pressure than the pressure at which the melamine off-gas is obtained. To this end, the pressure of the off-gas is reduced typically by 2-10 bar. In connection herewith, the system of the invention comprises a pressure reducing unit downstream of an outlet for the melamine off-gas, and upstream of a section for the condensation of the off-gas. The invention also includes a method for the modernization of an integrated system for the production of melamine and urea. This is accomplished by adding the aforementioned pressure reducing unit to a pre-existing system.

22 Claims, 3 Drawing Sheets

METHOD AND SYSTEM FOR THE INTEGRATED PRODUCTION OF UREA AND MELAMINE

CROSS-REFERENCE TO RELATED APPLICATIONS

This application is the national phase of PCT application PCT/NL2016/050291 having an international filing date of 25 Apr. 2016, which claims benefit of European patent application No. 15164888.8 filed 23 Apr. 2015. The contents of the above patent applications are incorporated by reference herein in their entirety.

FIELD OF THE INVENTION

The invention is in the field of the combined (integrated) production of urea and melamine. Particularly, the invention pertains to a method for the production of urea, whereby off-gas from the production of melamine is used as a feed to the synthesis of urea. The invention also pertains to an integrated system for the production of urea and melamine.

BACKGROUND OF THE INVENTION

Urea is generally produced from ammonia and carbon dioxide. It can be prepared by introducing an ammonia excess together with carbon dioxide at a pressure between 12 and 40 MPa and at a temperature between 150° C. and 250° C. into a urea synthesis section. In urea technology this is generally referred to as "high pressure" (HP). The resulting urea formation can be presented best in the form of two consecutive reaction steps, in the first step ammonium carbamate being formed according to the exothermic reaction:

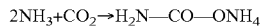

$$2NH_3 + CO_2 \rightarrow H_2N\text{---}CO\text{---}ONH_4$$

after which the ammonium carbamate formed is dehydrated in the second step to give urea according to the endothermic equilibrium reaction:

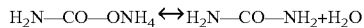

$$H_2N\text{---}CO\text{---}ONH_4 \leftrightarrow H_2N\text{---}CO\text{---}NH_2 + H_2O$$

Typical urea production plants further comprise a recovery section and a finishing section. In the recovery section non-converted ammonia and carbon dioxide are recovered and recirculated to the synthesis section. The recovery section is generally followed by an evaporation section. Therein the urea concentration is further increased by the evaporation of water, resulting in a highly concentrated solution that is generally referred to as a urea melt. In the finishing section, typically, the urea melt is brought into a desired solid, particulate form, generally involving techniques such as prilling, granulation, or pelletizing.

Melamine is regularly produced from urea according to the following reaction equation:

$$6\ (NH_2)_2CO \rightarrow C_3H_6N_6 + 6\ NH_3 + 3\ CO_2.$$

Generally two technologies exist for the production of melamine. One is a catalytic "low pressure" process, which applies atmospheric pressure (from atmospheric pressure to about 1 MPa). The other is called a "high pressure" process. In melamine production, high pressure refers to a pressure of at or above about 70 bar (7 MPa), more typically at or above 80 bar (8 MPa). The off-gases from the high pressure process generally have a pressure of from 1 to 4 MPa. It should be noted that, in urea technology, these pressures are within a range normally referred to as a "medium pressure ("MP")".

It is well-known in the art to combine the production of urea and the production of melamine. Thereby, generally, at least part or all of the urea produced in a urea plant, is sent to a melamine plant as a starting material. The production of melamine yields an off-gas comprising ammonia ($NH_3$) and carbon dioxide ($CO_2$) in a 2:1 stoichiometric ratio, which corresponds to that of the reactants in urea synthesis. Thus, the integrated production of urea and melamine typically involves feeding an ammonia and carbon dioxide containing gas stream obtained from the melamine plant, directly or indirectly to the synthesis section of the urea plant.

A method of the aforementioned type is disclosed in EP 1716111 B1 and is illustrated in the block diagram as given in FIG. 1. In this process the gas stream from the melamine plant is fed to an off-gas condensation section together with the carbamate formed in the recirculation section of a urea plant. This off-gas condensation section comprises at least one condenser apparatus. Upstream of the condenser apparatus, the off-gas from the melamine plant is mixed with the carbamate aqueous solution formed in the recirculation section of the urea plant. Alternatively, said off gas and carbamate aqueous solution are separately added to this condenser apparatus.

A connection, particularly a direct fluid connection, between a gaseous stream from one process system, viz. here the off-gas from a melamine plant, and another process system, viz. here the carbamate stream in the condensation section of the urea plant, is prone to cause in general a process disorder in the upstream processing of the former gas stream (i.e., the off-gas stream from the melamine plant. If the pressure in said condensation section increases, the pressure of the added off-gas from the melamine plant should increase as well, in order to obtain a positive flow. However an increase and fluctuation of the pressure in the melamine processing upstream of the-off gas, is possible only to a limited extent. Such a pressure increase causes a process disorder, and finally product losses in the melamine plant.

Further, it is noted that a urea plant normally obtains heat energy from, inter alia, the necessary compression of carbon dioxide. In the event that a urea plant is to directly process the gaseous stream formed in the melamine plant, which comprises carbon dioxide, less carbon dioxide will be subjected to compression, and thus additional heat energy will be required. This is especially the case for urea plants according the carbon dioxide stripping process. As a result, the energy consumption of the urea plant, typically expressed in steam consumption (kilogram steam per produced ton of urea product), increases by an increasing capacity of the coupled melamine facility. Hence, this provides an additional reason for the importance of improving the process economy of a system in which urea and melamine plants are coupled. It will be understood that a more stable process will generally be more economical.

Another issue in relation to systems in which an aqueous carbamate condensate is obtained and circulated to urea synthesis, relates to the amount of water. With reference to the above reaction equations for the synthesis of urea, it will be clear that the additional presence of water would shift the equilibrium to the side of the starting materials. Desirably, the amount of water is as high as necessary to have a transportable carbamate solution, but as low as possible in order to send as little water as possible to the urea synthesis section. The presence of an additional off-gas condensation section, such as in EP 1716111, therefore bears a risk of carrying unwanted additional water to the synthesis section.

SUMMARY OF THE INVENTION

In order to better address one or more of the foregoing desires, the invention, in one aspect provides an integrated process for the production of urea and melamine, the process comprising (a) subjecting ammonia and carbon dioxide to urea forming conditions so as to obtain an aqueous urea synthesis solution;

(b) subjecting said urea synthesis solution to recovery of non-reacted ammonia an carbon dioxide, thereby obtaining aqueous carbamate solution and urea;

(c) producing melamine in a melamine plant, whereby off-gas resulting from the melamine synthesis is obtained at a pressure of 15 to 35 bar;

(d) feeding obtained urea to the melamine plant as a starting material for producing the melamine;

(e) condensing said off-gas in the presence of water so as to form an aqueous carbamate solution;

(f) recycling carbamate obtained from said off-gases and carbamate obtained from said urea recovery section to the urea synthesis section as a starting material in producing urea;

wherein prior to condensation the pressure of the off-gas is reduced so as to be controlled at a pressure in a range of from 2 bar to 10 bar lower than the pressure at which the off-gas is obtained.

In another aspect, the invention presents a system for the production of urea and melamine, said system comprising a urea production zone; said urea production zone comprising a high pressure urea synthesis section and, downstream thereof and in fluid communication therewith, a low pressure urea recovery section adapted to separately obtain a urea solution and an aqueous carbamate solution; the system further comprising a melamine production zone; said melamine production zone comprising a high pressure melamine synthesis section and, downstream thereof and in fluid communication therewith, a melamine off-gas treatment section for obtaining melamine off-gas; said production zones being connected with each other so as to allow transport of urea solution obtained from the recovery section, preferably via an evaporation section, to the melamine synthesis section and to allow transport of melamine off-gas from the melamine off-gas treatment section to the urea production zone, whereby the urea production zone comprises a medium pressure condensation section adapted to receive said melamine off-gas, said condensation section having an outlet for condensed carbamate which is in fluid communication with an inlet of the urea synthesis section and in fluid communication therewith, wherein a pressure control device is provided between the melamine off-gas treatment section and the medium pressure condensation section.

In a further aspect, the invention is a method for the modernization of a urea plant comprising a high pressure urea synthesis section and, downstream thereof and in fluid communication therewith, a low pressure urea recovery section adapted to separately obtain a urea solution and an aqueous carbamate solution, the method comprising connecting the urea plant with a melamine plant comprising a high pressure melamine synthesis section and, downstream thereof and in fluid communication therewith, a melamine off-gas treatment section for obtaining melamine off-gas; said plants being connected with each other so as to allow transport of urea solution obtained from the urea recovery section, preferably via an evaporation section, to the melamine synthesis section and to allow transport of melamine off-gas from the melamine off-gas treatment section to the urea plant, the method further comprising adding a medium pressure condensation section adapted to receive said melamine off-gas, said condensation section having an outlet for condensed carbamate which is in fluid communication with an inlet of the urea synthesis section, and providing a pressure reducing device between the melamine off-gas treatment section and said medium pressure condensation section.

In a still further aspect, the invention provides a method for the modernization of a pre-existing system for the production of urea and melamine, said pre-existing system comprising a urea production zone and a melamine production zone; said urea production zone comprising a high pressure urea synthesis section in fluid communication with a low pressure urea recovery section adapted to separately obtain a urea solution and an aqueous carbamate solution, and, downstream thereof and in fluid communication therewith via a pressure increasing device (such as a pump), a medium pressure condensation section; said melamine production zone comprising a high pressure melamine synthesis section and, downstream thereof and in fluid communication therewith, a melamine off-gas treatment section for obtaining melamine off-gas; said production zones being connected with each other so as to allow transport of urea solution obtained from the urea recovery section, preferably via an evaporation section, to the melamine synthesis section and to allow transport of melamine off-gas from the melamine off-gas treatment section to the medium pressure condensation section, the method comprising providing a pressure control device, adapted to be used as a pressure reducing unit, between the melamine off-gas treatment section and the medium pressure condensation section.

DETAILED DESCRIPTION OF THE INVENTION

Figure 1:
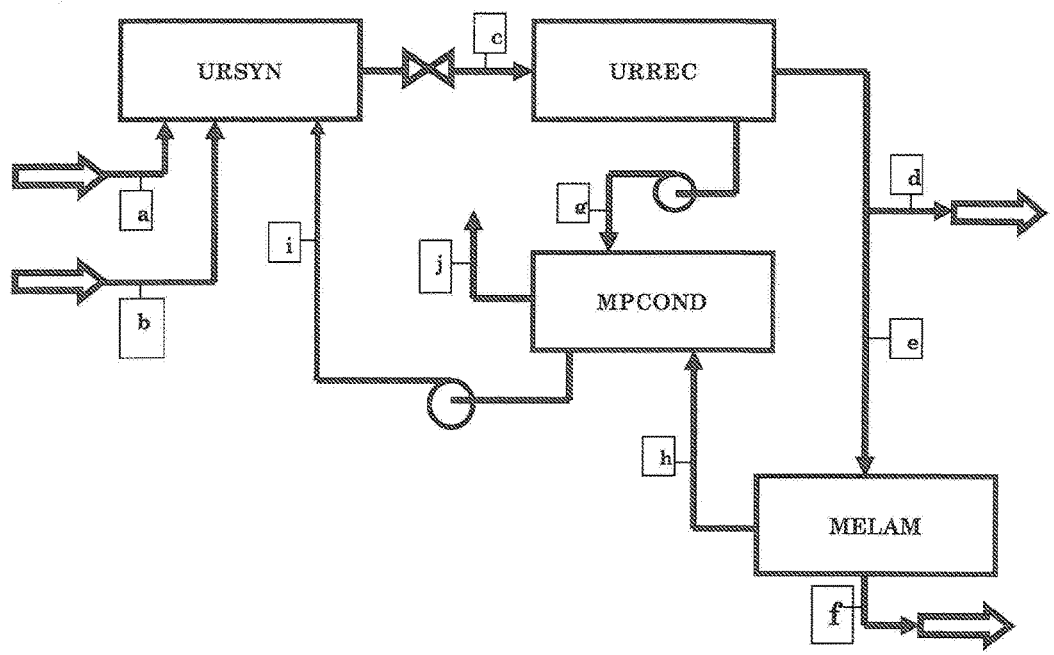
FIG. 1 is a schematic drawing of an integrated system for the production of urea and melamine in accordance with the prior art.

The invention is based on the insight to conduct the integration of the production of urea and melamine such, that effectively a decoupling between the processes achieved. In conventional systems for the integrated production of melamine and urea, the process variations (e.g. instabilities during operation, such as pressure fluctuations) in one process, will affect the other process.

To this end, the invention judiciously avoids the teaching of EP 1716111, according to which the off-gases coming from the melamine plant are fed to an off-gas condensation section operated at a pressure substantially equal to the pressure of said of-gases. In accordance with the present invention, this is accomplished by the introduction of a pressure-reducing step between the step of obtaining the ammonia and carbon dioxide as output from the melamine plant (i.e. the off-gases as obtained from the off-gas treatment section of the melamine plant) and the step of introducing the ammonia and carbon dioxide as input into the urea plant (i.e., the off-gases as fed into a medium pressure condensation section of the urea plant). Thereby the pressure is controlled in a range of from 2 bar to 10 bar lower than the pressure at which the off-gas is obtained.

In the process of the invention, the urea can be synthesized by any suitable method. A frequently used process for the preparation of urea according to a stripping process is the carbon dioxide stripping process as for example described in Ullmann's Encyclopedia of Industrial Chemistry, Vol. A27, 1996, pp 333-350. In this process, the synthesis section is followed by one or more recovery sections. The synthesis section comprises a reactor, a stripper, a condenser and a scrubber in which the operating pressure is in between 12 and 18 MPa and preferably in between 13 and 16 MPa. In the synthesis section the urea solution leaving the urea reactor is fed to a stripper in which a large amount of non-converted ammonia and carbon dioxide is separated from the aqueous urea solution. Such a stripper can be a shell and tube heat exchanger in which the urea solution is fed to the top part at the tube side and a carbon dioxide feed to the synthesis is added to the bottom part of the stripper. At the shell side, steam is added to heat the solution. The urea solution leaves the heat exchanger at the bottom part, while the vapor phase leaves the stripper at the top part. The vapor leaving said stripper contains ammonia, carbon dioxide and a small amount of water. Said vapor is condensed in a falling film type heat exchanger or a submerged type of condenser that can be a horizontal type or a vertical type. A horizontal type submerged heat exchanger is described in Ullmann's Encyclopedia of Industrial Chemistry, Vol. A27, 1996, pp 333-350. The heat released by the exothermic carbamate condensation reaction in said condenser is usually used to produce steam that is used in a downstream urea processing section, generally indicated as being an evaporation section, for heating and concentrating the urea solution. Since a certain liquid residence time is created in a submerged type condenser, a part of the urea reaction takes already place in said condenser. The formed solution, containing condensed ammonia, carbon dioxide, water and urea together with the non-condensed ammonia, carbon dioxide and inert vapor is sent to the reactor. In the reactor the above mentioned reaction from carbamate to urea approaches the equilibrium. The ammonia to carbon dioxide molar ratio in the urea solution leaving the reactor is generally in between 2.5 and 4 mol/mol. It is also possible that the condenser and the reactor are combined in one piece of equipment. An example of this piece of equipment as described in Ullmann's Encyclopedia of Industrial Chemistry, Vol. A27, 1996, pp 333-350. The formed urea solution leaving the urea reactor is supplied to the stripper and the inert vapor containing non-condensed ammonia and carbon dioxide is sent to a scrubbing section operating at a similar pressure as the reactor. In that scrubbing section the ammonia and carbon dioxide is scrubbed from the inert vapor. The formed carbamate solution from the downstream recovery system is used as absorbent in that scrubbing section. The urea solution leaving the stripper in this synthesis section requires a urea concentration of at least 45% by weight and preferably at least 50% by weight to be treated in one single recovery system downstream the stripper. The recovery section comprises a heater, a liquid/gas separator and a condenser. The pressure in this recovery section is between 200 to 600 kPa. In the heater of the recovery section the bulk of ammonia and carbon dioxide is separated from the urea and water phase by heating the urea solution. Usually steam is used as heating agent. The urea and water phase, contains a small amount of dissolved ammonia and carbon dioxide that leaves the recovery section and is sent to a downstream urea processing section where the urea solution is concentrated by evaporating the water from said solution.

The invention is not limited to any particular urea production process. Other processes and plants include those that are based on technology such as total recycle plants, the HEC process developed by Urea Casale, the ACES process developed by Toyo Engineering Corporation and the process developed by Snamprogetti. All of these processes, and others, may be used in the method of the invention.

In the process of the invention, the melamine is synthesized according to any method resulting in off-gases having a pressure in a range of from 15 to 35 bar, typically from a high pressure melamine production process. Such processes are described in Ullmann's Encyclopedia of Industrial Chemistry; Melamine and Guanamines, 2002, vol. 22, 377-392.

In the present description, reference is made to off-gas resulting from the melamine synthesis, which is obtained at a pressure of 15 to 35 bar. It will be understood that the off-gas directly resulting from high pressure melamine synthesis, will have a much higher pressure. In a regular melamine plant, the off-gas coming from synthesis is further treated and is then obtained, at the battery limits of the melamine plant, at said pressure of 15 to 35 bar.

It should be noted that the meaning of the terms "low pressure" (LP), "medium pressure" (MP), and "high pressure" (HP) is known to the skilled person. Particularly, in respect of urea production, HP indicates generally a pressure of from 12-40 MPa (120 to 400 bar), preferably 140 to 160 bar. In respect of melamine production HP generally indicates at or above 7 MPa (70 bar), preferably at or above 8 MPa (80 bar), and more preferably 80 to 150 bar. In respect of urea production, MP generally indicates pressures in a range of from 1 MPa to 8 MPa, preferably 1 MPa to 4 MPa (10-40 bar), more preferably 15 to 35 bar, and most typically 20 to 25 bar, LP in urea production stands for pressures below 1 MPa, preferably 0.3-0.5 MPa (3-5 bar), preferably about 4 bar.

The process of the invention involves using urea produced in the urea plant as a starting material in the melamine synthesis. Depending on the mutual plant capacities, this can be all of the urea produced in the urea plant, or a part of it. In the event that not all of the produced urea is used in the melamine production, the remainder of the urea can be subjected to regular urea finishing, e.g. obtained as granules or prills. Also, such urea can be obtained as an aqueous solution, such a solution having 30-35 wt. % of urea and of sufficient purity so as to be suitable as so-called Diesel Exhaust Fluid (DEF). These and other finished urea products are known to the skilled person, and do not require elucidation here.

Off-gas resulting from the melamine synthesis (as mentioned comprising $NH_3$ and $CO_2$ in a 2:1 ratio) is eventually put to use as a starting material for urea synthesis. This is done in a specific manner in accordance with the invention. The off-gas is generally obtained, in a melamine plant, at a pressure of 15 to 35 bar. These pressures are lower than those of the melamine synthesis itself. This is a result from one or more regular purification (washing) steps to which the raw off-gas is normally subjected.

The off-gas as obtained from melamine synthesis is subjected to condensation in the presence of water so as to form an aqueous carbamate solution. This aqueous carbamate is recycled back to urea synthesis, in conventional manner. In the urea production process, from low pressure recovery, also aqueous carbamate is recycled to urea synthesis. This aqueous carbamate is preferably combined with the melamine off-gas recycle fluid. This can be before or after condensation of the off-gas.

The off-gas from melamine synthesis can be obtained, typically as a result of downstream processing or work-up, such as a washing step so as to comprise a substantial amount of water, such as 3 to 40% by weight and more specifically between 5 and 30% by weight, next to the ammonia and carbon dioxide. In that event, the required water is provided by the composition of the off-gas itself, and the condensation can be in the absence of the aqueous carbamate solution from the urea plant. It is also conceivable that part of the aqueous carbamate from urea recovery is used in the condensation of the melamine off-gas, and part is directly sent to urea synthesis.

In an interesting embodiment of the process according to the invention, the water in the presence of which the off-gas is condensed, comprises water obtained from adiabatic expansion of the aqueous urea synthesis solution. To this end, the urea production zone suitably comprises a unit for subjecting a synthesis solution obtained from the urea synthesis section to adiabatic expansion, such as a flash vessel. This unit is positioned downstream of the urea synthesis section and upstream of the urea recovery section, and in fluid communication with both sections. It will be understood that, in order to be able to use the vapor released from adiabatic expansion in the condensation of the melamine off-gas, the unit for adiabatic expansion has a gas outlet adapted to transport said vapor to a medium pressure condensation section wherein the melamine off-gas is condensed.

The amount of water preferably is sufficiently high so as to avoid crystallization of carbamate. To this end, a preferred minimum amount of water can be defined, depending on the pressure at which the condensation takes place. As indicated above, the condensation takes place at medium pressure (MP). As mentioned, MP generally indicates pressures in a range of from 1 MPa to 8 MPa, preferably 1 MPa to 4 MPa (10-40 bar), more preferably 15 to 35 bar, and most typically of from 20 bar to 25 bar. In the process of the invention, the condensation most preferably takes place at a pressure in a range of from 20 bar to 22 bar. Table 1 indicates the preferred minimum amount of water in the formed carbamate related to a range of MP condensation pressures in order to prevent crystallization of said carbamate.

TABLE 1

| Condensation Pressure [bar] | Preferred minimum water content [wt. %] |
| --- | --- |
| 10 | 26.9 |
| 12 | 25.5 |
| 14 | 24.1 |
| 16 | 22.8 |
| 18 | 21.4 |
| 20 | 20.0 |
| 22 | 18.6 |
| 24 | 17.3 |
| 26 | 15.9 |
| 28 | 14.5 |
| 30 | 13.1 |

The invention is based on the surprisingly simple, but effective, step of subjecting the melamine off-gas to pressure reduction prior to condensation. This reduction of pressure is generally of from 2 bar to 10 bar relative to the pressure at which the off-gas is obtained. Preferably, the pressure is reduced by 2 to 5 bar, more preferably by 3-4 bar. Said reduction of pressure is believed to result in a decoupling of the processes in the melamine and urea plants, whilst retaining the integration of the two processes and plants. As a result, variations in pressure in either of the plants, will not affect the operation in the other plant (i.e., avoiding pressure changes and swings that would prevent the plant from smooth operation).

The pressure reduction is conducted so as to control the pressure of the gas sent to the condensation section to a pressure within a range of from 2 bar to 10 bar below the pressure at which the off-gas is obtained. The controlling of the pressure does not necessarily involve rectifying the pressure of the gas subjected to condensation to a constant value. Accordingly, the controlled pressure can involve a margin, such as 2 to 10 bar, preferably 2 to 5 bar, and more preferably 3-4 bar. It is, however, preferred to control the pressure of the gas sent to condensation so as to be rectified at a single, fixed value, said value being any one within the aforementioned ranges of pressure reduction. Preferred absolute pressure values for the gas sent to condensation are 18-24 bar, preferably 20-22 bar.

Preferably, the reduction of pressure is applied downstream of the melamine plant, i.e., outside of the battery limits thereof. It is also possible, however, to reduce the pressure still within the battery limits of the melamine plant. The pressure is generally reduced by passing the off-gas through a pressure reduction valve. Such a pressure reduction valve can control the required reduced pressure in the condensation zone.

The foregoing means that the section in which the off-gas is subjected to condensation, is operated at a pressure of 2-10 bar lower than that at which the off-gas is obtained. As said, this condensation is possibly together with aqueous carbamate obtained from urea recovery. To this end, the pressure of the aqueous carbamate from urea recovery will be increased. It will be understood that this can be regularly done by means of a pressure pump.

The invention also pertains to a system for the production of urea and melamine in accordance with the method as described above. Said system comprises a urea production zone. This can be a separate urea plant, or it can be a zone that is part of an integrated plant for the production of urea and melamine. The urea production zone comprises a high pressure urea synthesis section and, downstream thereof and in fluid communication therewith, a low pressure urea recovery section adapted to separately obtain urea and an aqueous carbamate solution. The system also comprises a melamine production zone which, again, can be a separate plant or a zone comprised in an integrated plant. The melamine production zone comprises a high pressure melamine synthesis section. It will be understood that the term "high pressure" has different meanings in respect of the urea production zone and the melamine production zone, as explained hereinbefore. Downstream of the melamine production zone, and in fluid communication therewith, the system comprises a melamine off-gas treatment section for obtaining melamine off-gas. The production zones are connected with each other so as to allow transport of urea solution obtained from the urea recovery section, preferably via an evaporation section, to the melamine synthesis section and to allow transport of melamine off-gas from the melamine off-gas treatment section to the urea production zone.

As the skilled person will be aware, the urea solution obtained from the recovery section will generally be subjected to concentration prior to being used as a starting material in melamine synthesis. As mentioned before, this concentration will preferably occur to the extent that a highly concentrated urea solution is formed (e.g. having more than 90 wt. % of urea, such as more than 95 wt. % of urea, such as more than 99 wt. % of urea) for which the term "urea melt" is used in the art. It will be understood that such concentration occurs between urea recovery and melamine synthesis, and preferably in an evaporation section of the urea plant. Typically, the urea solution is concentrated in an evaporation section to a urea melt having a final moisture content of 0.2-5.0% by weight.

The urea production zone comprises a medium pressure condensation section adapted to receive said melamine off-gas. This condensation section is provided with an outlet for condensed carbamate which is in fluid communication with an inlet of the synthesis section. In this respect, the condensation section can be considered to be upstream of the urea synthesis section and in fluid communication therewith. However, it will be understood that the urea synthesis and recirculation process is conducted as a loop. I.e., viewed from the condensed carbamate, the aforementioned condenser is upstream of the urea synthesis section. However, when viewed from the non-reacted gases recovered in the recirculation section, downstream of the synthesis section, also the condenser can be considered to be downstream of the synthesis section.

In accordance with the invention, a pressure control device (pressure control unit), adapted to be used as a pressure reducing unit, is provided between the melamine off-gas treatment section and the medium pressure condensation section. Such a unit is typically an orifice or a valve, and preferably a pressure reducing valve.

In a further aspect, the invention provides a method for the modernization of a pre-existing system for the production of urea and melamine. This refers to a pre-existing system preferably such as disclosed in EP1716111. The pre-existing system comprises a urea production zone (such as a urea plant) and a melamine production zone (such as a melamine plant of the high pressure type). The urea production zone comprises a high pressure urea synthesis section in fluid communication with a low pressure urea recovery section adapted to separately obtain urea and an aqueous carbamate solution, and, downstream thereof and in fluid communication therewith via a pressure increasing unit (such as a pump), a medium pressure condensation section. The melamine production zone comprises a high pressure melamine synthesis section and, downstream thereof and in fluid communication therewith, a melamine off-gas treatment section for obtaining melamine off-gas.

The production zones are connected with each other so as to allow transport of urea solution obtained from the urea recovery section, preferably via an evaporation section, to the melamine synthesis section and to allow transport of melamine off-gas from the melamine off-gas treatment section to the medium pressure condensation section, substantially as discussed above. The modernization method of the invention resides therein that one provides a pressure control device, adapted to be used as a pressure reducing unit, between the melamine off-gas treatment section and the medium pressure condensation section.

In a preferred embodiment, the modernization method of the invention further comprises adding, to the urea production zone, a unit adapted to subject a synthesis solution obtained from the urea synthesis section to adiabatic expansion. This unit is added downstream of the urea synthesis section and upstream of the urea recovery section, and in fluid communication with both sections. The unit for adiabatic expansion is provided with a gas outlet adapted to transport vapor released by adiabatic expansion to the medium pressure condensation section.

The invention is further illustrated with reference to the drawings. It will be understood that the drawings are not limiting the invention. E.g., the invention is not limited to the specific types of equipment and specific plant systems as shown. All figures show schematic drawings of equipment parts and process streams relating to embodiments of the invention.

FIG. 1 is a schematic drawing of an integrated system for the production of urea and melamine in accordance with EP 1716111.

Carbon dioxide and ammonia are introduced via respectively line (a) and line (b) as a feedstock to the urea synthesis section (URSYN) in the urea plant. The urea solution leaving the urea synthesis section is expanded and added via line (c) to a recirculation section (URREC) that is operated at a pressure that s substantially lower than the pressure in the urea synthesis section. In this example the pressure in the recirculation section is in the order of magnitude of 0.4 MPa. In this recirculation section (URREC) the bulk of the present non-condensed ammonia and carbon dioxide is separated from the aqueous urea solution. This separated ammonia and carbon dioxide is subsequently condensed to form an aqueous carbamate solution.

The urea solution leaving the recirculation section (URREC) is concentrated (not shown in the diagram) usually in an evaporation section to a urea melt that is suitable to be used as a feedstock for the melamine plant (MELAM). This concentrated urea melt is sent via line (e) to the melamine plant (MELAM) and can be but not necessarily partly sent via line (d) to i.e. a urea finishing section to obtain a urea product that is suitable as fertilizer.

In the melamine plant (MELAM) the urea is used as feedstock for the melamine product according the following formula:

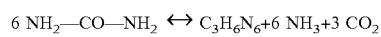

The non-converted gaseous ammonia and carbon dioxide is returned to the urea plant (line h) via a newly installed off gas condensation section (MPCOND). This off gas condensation section consists of at least one condenser. The pressure of said vapor that is returned to the urea plant is 1 to 4 MPa and more specifically 1.5 to 3.5 MPa. This vapor may comprise next to the ammonia and carbon dioxide also water. The pressure in the newly installed off gas condensation section (MPCOND) is substantially equal to the pressure of the vapor arriving from the melamine plant (MELAM). The vapor from the melamine plant is condensed in the presence of the carbamate solution that is formed in said recirculation section from the urea plant (URREC) via line (g). The released condensation heat is usually dissipated in cooling water. The formed carbamate solution in the off gas condensation section (MPCOND) comprising a smaller water concentration in comparison to the water concentration in the carbamate solution that is added to said off gas condensation, is conveyed via line (i) to the synthesis section in the urea plant. Vapor comprising non-condensed ammonia and carbon dioxide leaving the off gas condensation section (MPCOND) via line (j) is processed in the downstream processing in the urea plant (not indicated) and results in an increased load of the waste water treatment section (not indicated) of the urea plant.

Figure 2:
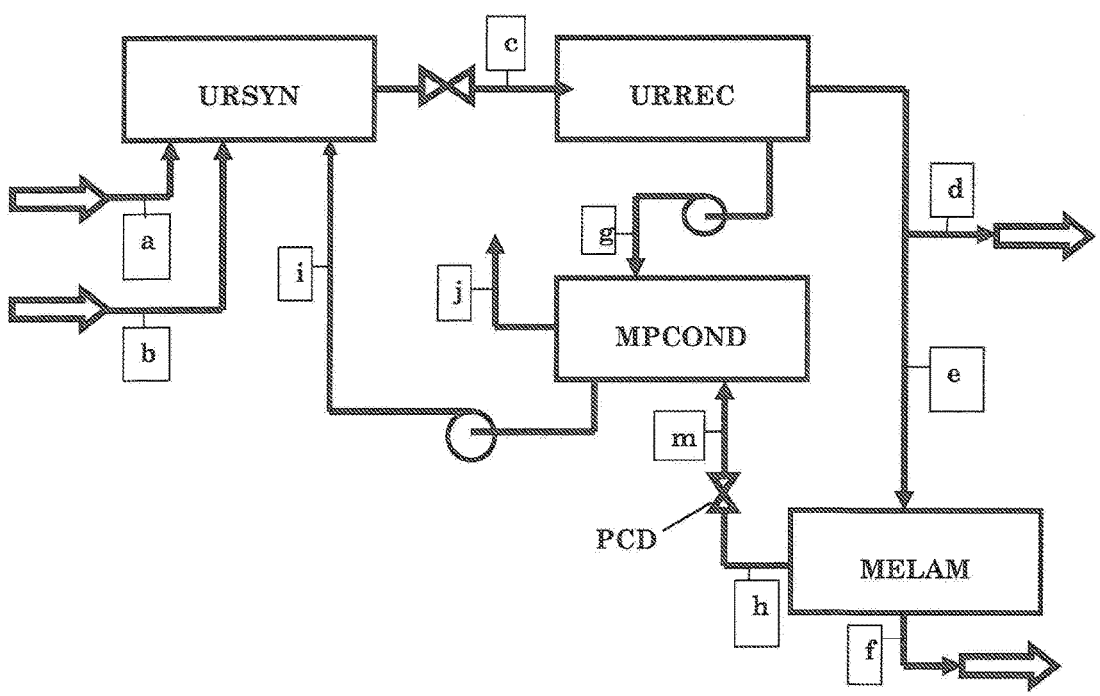
FIGS. 2-4 are schematic drawings of integrated systems for the production of urea and melamine in accordance with embodiments of the invention.

FIG. 2 is a schematic drawing of an embodiment of an integrated system for the production of urea and melamine in accordance with the invention. The equipment parts and flow lines have the same meaning as in FIG. 1. In the present embodiment of the invention, the pressure at which the off gas condensation (MPCOND) takes place is substantially lower than the pressure at which the vapor is released from the melamine plant (MELAM). Said released vapor from the melamine plant via line (h) is reduced in pressure by 0.2 to 1 MPa by using a pressure control device (PCD) which is usually a control valve. The vapor reduced in pressure is discharged via line (m) into the off gas condensation (MPCOND) which operates at a substantially equal pressure. Said vapor can be mixed with the carbamate solution from line (g) before the formed liquid/vapor mixture enters the off gas condensation section (MPCOND) or is introduced separately from said carbamate solution into the off gas condensation section (MPCOND).

Figure 3:
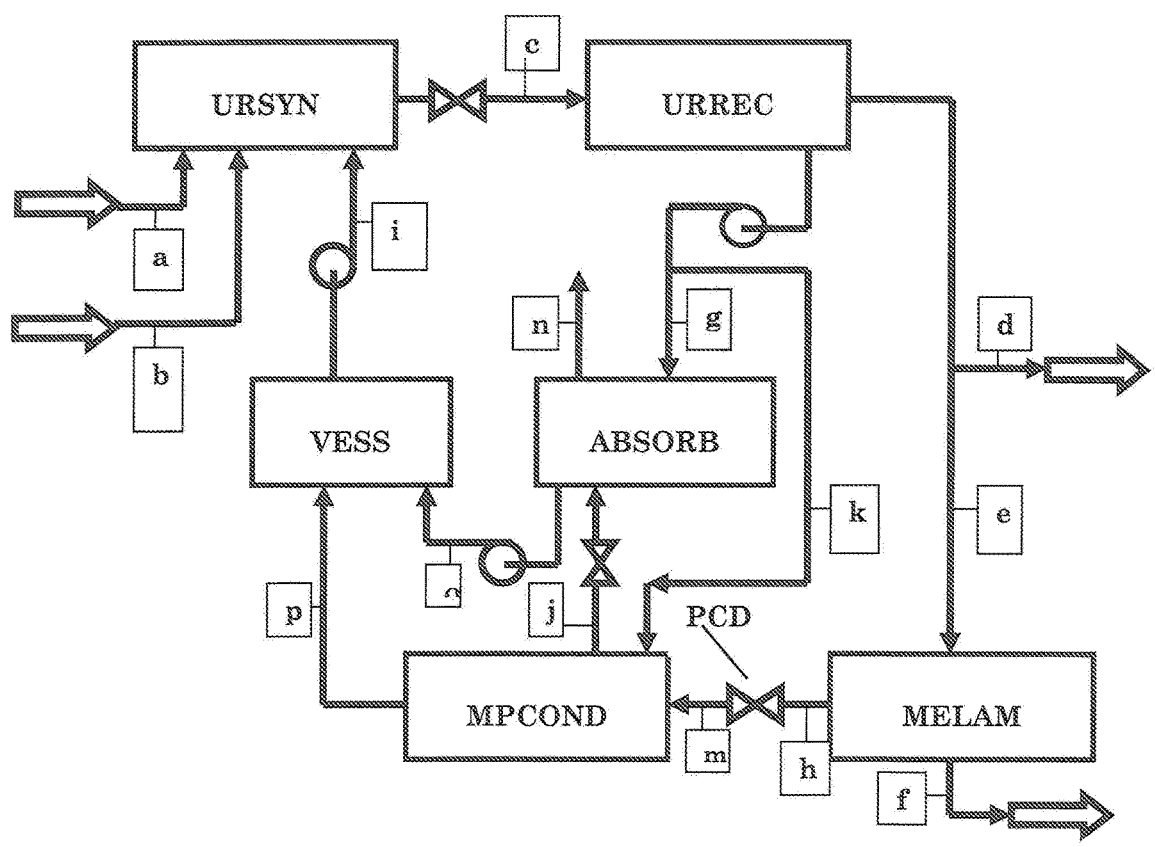

FIG. 3 is a schematic drawing of another embodiment of an integrated system for the production of urea and melamine in accordance with the invention. This scheme pertains to a melamine plant the vapor released from which contains a substantial amount of water, such as in a concentration of typically 5 to 30% by weight.

Carbon dioxide and ammonia are introduced via respectively line (a) and line (b) as a feedstock to the urea synthesis section (URSYN) in the urea plant. The urea solution leaving the urea synthesis section is expanded and added via line (c) to a recirculation section (URREC) that is operated at a pressure that is substantially lower than the pressure in the urea synthesis section. In this example the pressure in the recirculation section is in the order of magnitude of 0.4 MPa. In this recirculation section (URREC) the bulk of the present non-condensed ammonia and carbon dioxide is separated from the aqueous urea solution. This separated ammonia and carbon dioxide is subsequently condensed to form an aqueous carbamate solution.

The urea solution leaving the recirculation section (URREC) is concentrated (not shown in the diagram) in an evaporation section to a urea melt that is suitable to be used as a feedstock for the melamine plant (MELAM). This concentrated urea melt is sent via line (e) to the melamine plant (MELAM) and can be but not necessarily partly sent via line (d) to i.e. a urea finishing section to obtain a urea product that is suitable as fertilizer.

The non-converted gaseous ammonia and carbon dioxide from the melamine plant, typically containing the aforementioned substantial amount of water is returned to the urea plant (line m) after it is reduced in a pressure by a pressure control device (PCD). The pressure is substantially lower than the pressure at which said vapor is released from the melamine plant via line (h). The vapor leaving the melamine plant arriving in the off gas condensation section via line (m) can be mixed upstream said condensation section (MPCOND) with carbamate solution leaving the recirculation section of the urea plant via line (k) or can be separately introduced into said condensation section (MPCOND). The carbamate solution formed in the recirculation section (URREC) of the urea plant is partially sent to the off gas condensation section (MPCOND) via line (k). It is also possible that the amount of said carbamate solution sent to said off gas condensation section is zero.

The non-condensed ammonia and carbon dioxide vapor comprising small amounts of moisture leaving the off gas condensation section is sent via line (j) to an off gas absorption device (ABSORB). In this device said vapor is in countercurrent contact with carbamate solution leaving the recirculation section (URREC) of the urea plant via line (g). The non-condensed ammonia and carbon dioxide in said vapor is absorbed in said carbamate solution and vapor comprising very small amounts of ammonia and carbon dioxide are discharged via line (n) to the downstream processing in the urea plant for further purification. The carbamate solution leaving the off gas absorption (ABSORB) via line (o) is collected together with the formed carbamate solution leaving the off gas condensation section (MPCOND) via line (p) in a carbamate collecting vessel (VESS). The pressure in the off gas absorption (ABSORB) can be equal to or lower than the pressure in the off gas condensation section (MPCOND). The pressure in the off gas absorption (ABSORB) is higher than the pressure in the urea recirculation section (URREC) of the urea plant.

The collected carbamate solutions leaving the collecting vessel (VESS) is conveyed to the synthesis section (URSYN) of the urea plant via line (i).

Figure 4:
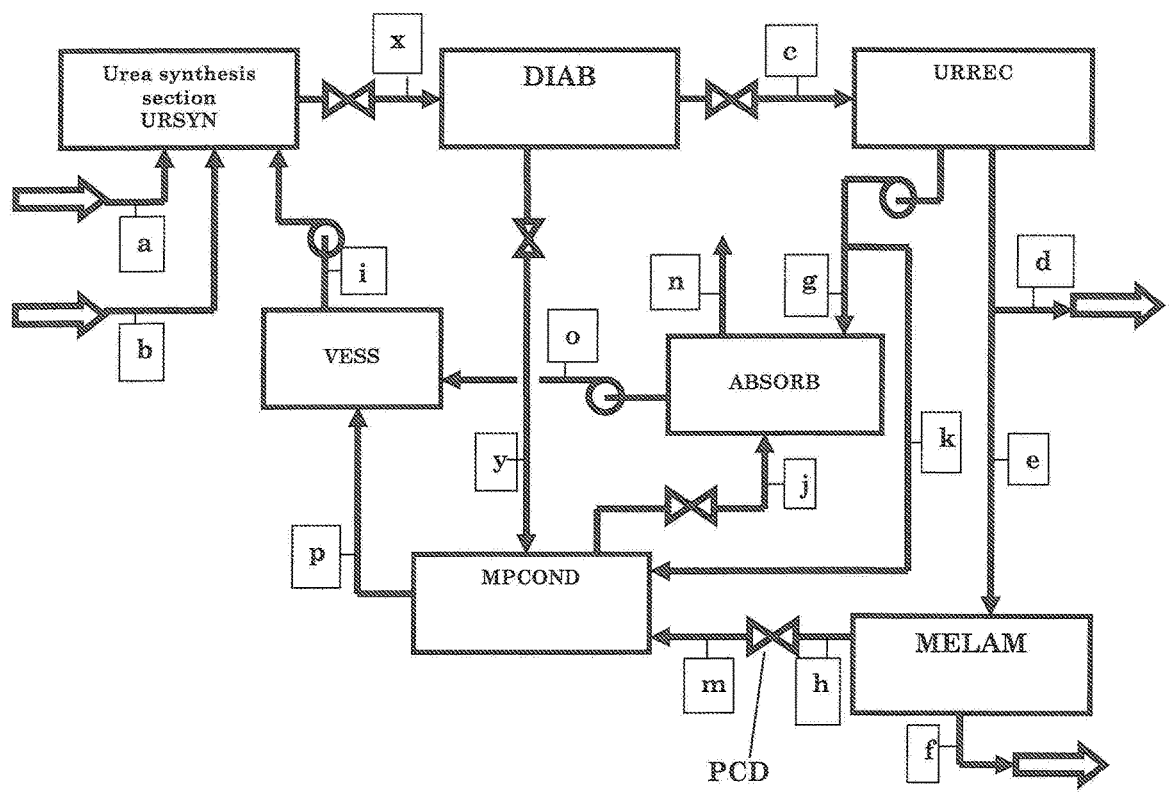

FIG. 4 is a schematic drawing of yet another embodiment of an integrated system for the production of urea and melamine in accordance with the invention. Again, this relates to a melamine plant releasing vapors that contain substantial amounts of water.

In most aspects this embodiment is similar to the embodiment as described in the example belonging to FIG. 3. In the present example however the urea solution leaving the urea synthesis section (URSYN) via line (x) is subjected to an adiabatic expansion step (DIAB) before said solution is subjected to the recirculation section (URREC) in the urea plant via line (c). The pressure in the expansion step (DIAB) is in between the operating pressure of the urea synthesis (URSYN) and the operating pressure of the off gas condensation section (MPCOND). The vapor released by the adiabatic expansion is discharged to the off gas condensation (MPCOND) via line (y). By the application of the adiabatic expansion step (DIAB) in between the urea synthesis section and the urea recirculation section, an OPEX reduction in comparison of the OPEX for a process concept according example 3 for the total urea plant is achieved. The achieved OPEX reduction is about 50 to 100 kg steam per produced tonne of urea. The quality of that steam is:

Pressure≈2.4 MPa
Temperature≈320° C.

While the invention has been illustrated and described in detail in the drawings and foregoing description, such illustration and description are to be considered illustrative or exemplary and not restrictive; the invention is not limited to the disclosed embodiments.

For example, it is possible that the released condensation heat in the condensation section (MPCOND) is used for pre-concentrating urea solutions usually exiting from the recirculation section. Also, it will be possible to couple two different urea plants to a single melamine plant. If so, e.g., urea from either or both of these plants can be fed to melamine synthesis, whilst the off-gas from melamine synthesis will be subjected to pressure reduction and condensation in accordance with the invention, with aqueous carbamate from one of the urea plants.

Other variations to the disclosed embodiments can be understood and effected by those skilled in the art in practicing the claimed invention, from a study of the drawings, the disclosure, and the appended claims In the claims, the word "comprising" does not exclude other elements or steps, and the indefinite article "a" or "an" does not exclude a plurality. The mere fact that certain features of the invention are recited in mutually different dependent claims does not indicate that a combination of these features cannot be used to advantage.

Where, in this description, it is spoken of "fluid communication", this refers to any connection, direct or indirect, between a first part or section of a plant and a second part or section of a plant via which fluids, notably liquids or gases, can flow from the first part of the plant to the second part of the plant. Such fluid communication is typically provided by piping systems, hoses, gas flow lines, or other devices well-known to the skilled person for the transportation of liquids and/or gases. From the process descriptions contained herein, it will be entirely clear in which events the fluids concerned are liquids or gases.

In sum, the invention includes an integrated process for the production of urea and melamine, as well as a system for carrying out the process. The invention thereby pertains to an integrated process of the type wherein off-gas obtained from the production of melamine is entered into the process for the production of melamine, by condensation in the presence of water. A typical embodiment thereof is the condensation in the presence of an aqueous carbamate solution obtained from urea recovery. In accordance with the invention, said condensation takes place at a substantially lower pressure than the pressure at which the melamine off-gas is obtained. To this end, the pressure of the off-gas is reduced typically by 2-10 bar. In connection herewith, the system of the invention comprises a pressure reducing unit downstream of an outlet for the melamine off-gas, and upstream of a section for the condensation of the off-gas. The invention also includes a method for the modernization of an integrated system for the production of melamine and urea. This is accomplished by adding the aforementioned pressure reducing unit to a pre-existing system.

The invention claimed is:

1. An integrated process for the production of urea and melamine, the process comprising:
   (a) subjecting ammonia and carbon dioxide to urea forming conditions so as to obtain an aqueous urea synthesis solution;
   (b) subjecting said urea synthesis solution to recovery of unreacted ammonia and carbon dioxide, thereby obtaining aqueous carbamate solution and urea;
   (c) producing melamine in a melamine plant, whereby off-gas resulting from the melamine synthesis is obtained at a pressure of 15 to 35 bar;
   (d) feeding obtained urea to the melamine plant as a starting material for producing the melamine;
   (e) condensing said off-gas in the presence of water so as to form an aqueous carbamate solution;
   (f) recycling carbamate obtained from said off-gas and carbamate obtained from said urea recovery section to the urea synthesis section as a starting material in producing urea;
   wherein prior to condensation the pressure of the off-gas is reduced so as to be controlled at a pressure in a range of from 2 bar to 10 bar lower than the pressure at which the off-gas is obtained.

2. The process of claim 1, wherein the reduction of pressure is conducted downstream of the melamine plant.

3. The process of claim 1, wherein the reduction of pressure is in a range of from 2 bar to 5 bar lower than the pressure at which the off-gas is obtained.

4. The process of claim 1, wherein the reduced pressure is controlled so as to be rectified with a margin of 2-5 bar.

5. The process of claim 1, wherein the pressure of the gas subjected to condensation is in a range of from 18 bar to 24 bar.

6. The process of claim 1, wherein the water in the presence of which the off-gas is condensed, comprises water vapor contained in the off-gas.

7. The process of claim 1, wherein the water in the presence of which the off-gas is condensed, comprises water contained in the aqueous carbamate solution obtained by recovery from the urea synthesis solution.

8. The process of claim 1, wherein the water in the presence of which the off-gas is condensed comprises water obtained from adiabatic expansion of the aqueous urea synthesis solution.

9. A system for the production of urea and melamine, said system comprising:
   (a) a urea production zone; said urea production zone comprising a high pressure urea synthesis section and, downstream thereof and in fluid communication therewith, a low pressure urea recovery section adapted to separately obtain a urea solution and an aqueous carbamate solution;
   (b) a melamine production zone; said melamine production zone comprising a high pressure melamine synthesis section and, downstream thereof and in fluid communication therewith, a melamine off-gas treatment section for obtaining melamine off-gas;
   said urea production zone and melamine zone being connected with each other so as to allow transport of urea solution obtained from the urea recovery section to the melamine synthesis section and to allow transport of melamine off-gas from the melamine off-gas treatment section to the urea production zone, wherein the urea production zone comprises a medium pressure condensation section adapted to receive said melamine off-gas, said condensation section having an outlet for condensed carbamate which is in fluid communication with an inlet of the urea synthesis section and in fluid communication therewith, and
   (c) a pressure control device between the melamine off-gas treatment section and the medium pressure condensation section.

10. The system of claim 9, comprising a connection from the urea recovery section to the medium pressure condensation section, said connection provided with a pressure control device, so as to allow feeding the aqueous carbamate solution from the recovery section to the medium pressure condensation section.

11. The system of claim 9, comprising, downstream of the urea synthesis section and upstream of the urea recovery section, and in fluid communication with both sections, a unit for subjecting a synthesis solution obtained from the urea synthesis section to adiabatic expansion, whereby the unit for adiabatic expansion has a gas outlet adapted to transport vapor released by adiabatic expansion to the medium pressure condensation section.

12. The system of claim 9, wherein the urea and melamine production zones are separate plants.

13. A method for the modernization of a urea plant comprising a high pressure urea synthesis section and, downstream thereof and in fluid communication therewith, a low pressure urea recovery section adapted to separately obtain a urea solution and an aqueous carbamate solution, the method comprising
   connecting the urea plant with a melamine plant comprising a high pressure melamine synthesis section and, downstream thereof and in fluid communication therewith, a melamine off-gas treatment section for obtaining melamine off-gas;
   said plants being connected with each other so as to allow transport of urea solution obtained from the urea recovery section to the melamine synthesis section and to allow transport of melamine off-gas from the melamine off-gas treatment section to the urea plant, the method further comprising adding a medium pressure condensation section adapted to receive said melamine off-gas, said condensation section having an outlet for condensed carbamate which is in fluid communication with an inlet of the urea synthesis section, and providing a pressure reducing device between the melamine off-gas treatment section and said medium pressure condensation section.

14. A method for the modernization of a pre-existing system for the production of urea and melamine, said pre-existing system comprising a urea production zone and a melamine production zone;

said urea production zone comprising a high pressure urea synthesis section in fluid communication with a low pressure urea recovery section adapted to separately obtain urea and an aqueous carbamate solution, and, downstream thereof and in fluid communication therewith via a pressure increasing unit, a medium pressure condensation section;

said melamine production zone comprising a high pressure melamine synthesis section and, downstream thereof and in fluid communication therewith, a melamine off-gas treatment section for obtaining melamine off-gas;

said production zones being connected with each other so as to allow transport of urea solution obtained from the urea recovery section to the melamine synthesis section and to allow transport of melamine off-gas from the melamine off-gas treatment section to the medium pressure condensation section;

the method comprising providing a pressure control device, adapted to be used as a pressure reducing unit, between the melamine off-gas treatment section and the medium pressure condensation section.

15. The process of claim 3, wherein the reduction of pressure is in a range of from 3 bar to 4 bar.

16. The process of claim 4, wherein the reduced pressure is controlled so as to be rectified with a margin of 3-4 bar.

17. The process of claim 5, wherein the pressure of the gas subjected to condensation is in a range of from 20 bar to 22 bar.

18. The system of claim 9, wherein the transport of urea solution obtained from the recovery section is via an evaporation section.

19. The method of claim 13, wherein transport of the urea solution obtained from the urea recovery section is via an evaporation section.

20. The method of claim 14, wherein the pressure increasing unit is a pump.

21. The method of claim 14, wherein the transport of urea solution obtained from the urea recovery section is via an evaporation section.

22. The method of claim 14, wherein the pressure increasing unit is a pump.

* * * * *